(12) United States Patent
Haase et al.

(10) Patent No.: US 8,431,890 B1
(45) Date of Patent: Apr. 30, 2013

(54) MASS SPECTROMETER WITH MALDI LASER SYSTEM

(71) Applicant: Bruker Daltonik GmbH, Bremen (DE)

(72) Inventors: Andreas Haase, Bremen (DE); Jens Hoehndorf, Bremen (DE)

(73) Assignee: Bruker Daltonik GmbH, Bremen (DE)

( * ) Notice: Subject to any disclaimer, the term of this patent is extended or adjusted under 35 U.S.C. 154(b) by 0 days.

(21) Appl. No.: 13/656,284

(22) Filed: Oct. 19, 2012

(51) Int. Cl.
  *H01J 49/00* (2006.01)
(52) U.S. Cl.
  USPC .......................................................... 250/288
(58) Field of Classification Search .................. 250/288, 250/281, 282, 423 P
  See application file for complete search history.

(56) References Cited

U.S. PATENT DOCUMENTS

| | | | |
|---|---|---|---|
| 7,235,781 B2 | 6/2007 | Haase et al. | |
| 7,385,192 B2 | 6/2008 | Haase et al. | |
| 7,408,152 B2 | 8/2008 | Holle et al. | |
| 2009/0197295 A1* | 8/2009 | Fournier et al. | 435/29 |

OTHER PUBLICATIONS

Dreisewerd, K., "The Desorption Process in MALDI", Chem. Rev. 2003, 395-425.

* cited by examiner

*Primary Examiner* — Kiet T Nguyen
(74) *Attorney, Agent, or Firm* — O'Shea Getz P.C.

(57) ABSTRACT

The invention relates to a mass spectrometer comprising a laser system for mass-spectrometric analysis with ionization of analyte molecules in a sample by matrix-assisted laser desorption. A mass spectrometer with a pulsed UV laser system produces a spatially distributed spot pattern with peaks of uniform energy density on the sample, increasing thereby the degree of ionization for analyte ions as compared to conventional spot patterns. The spot pattern with peaks of uniform energy density can be produced by homogeneous illumination of a pattern generator, for example a lens array. The homogeneous illumination can be generated by a low-cost beam-shaping element, which does not act on the UV beam but on the original infrared beam, in conjunction with changes to the beam cross-section and beam profile brought about by the nonlinear conversion crystals. This beam shaping not only produces a beam profile which illuminates the pattern generator homogeneously with low losses, but at the same time increases the efficiency of the frequency multiplication and the lifetime of the conversion crystals so that cost savings are achieved because less laser energy is required and the lifetime is increased.

13 Claims, 2 Drawing Sheets

MASS SPECTROMETER WITH MALDI LASER SYSTEM

PRIORITY INFORMATION

This patent application claims priority from German Patent Application No. 10 2011 116 405.0 filed on Oct. 19, 2011, which is hereby incorporated by reference in its entirety.

FIELD OF THE INVENTION

The invention relates to a mass spectrometer comprising a laser system for mass-spectrometric analyses with ionization of analyte molecules in a sample by matrix-assisted laser desorption.

BACKGROUND OF THE INVENTION

During the past twenty years, two methods have become established in the mass spectrometry of biological macromolecules: ionization by matrix-assisted laser desorption (MALDI), and electrospray ionization (ESI). The biological macromolecules to be analyzed are termed analyte molecules below. In the MALDI method, the analyte molecules are generally prepared on the surface of a sample support in a solid, polycrystalline matrix layer, and are predominantly ionized with a single charge, whereas in the ESI method they are dissolved in a liquid and are ionized with multiple charges. The two methods have made it possible to conduct mass-spectrometric analysis of biological macromolecules for genomic, proteomic and metabolomic investigations; their inventors, John B. Fenn and Koichi Tanaka, were awarded the Nobel Prize for chemistry in 2002.

In a MALDI sample preparation, there are $10^3$ to $10^5$ times as many matrix molecules as analyte molecules, and the matrix molecules form a polycrystalline layer in which the analyte molecules are integrated in the interior of the crystals or at their grain boundaries, largely without coming into contact with other analyte molecules. The matrix substance is selected in such a way that its molecules can absorb the ultraviolet light of the laser pulse, on the one hand, and can protonate the analyte molecules on the other. In the prior art, a small illumination area (called "spot" in the following), with a diameter of around 50 to 200 micrometers, on the prepared MALDI sample is briefly irradiated with a laser pulse that is strongly absorbed by the matrix molecules. The pulsed irradiation converts surface matrix material from the solid state into the plasma phase in only a few nanoseconds, during which many matrix molecules (or their fragments) are thermally ionized. The analyte molecules are usually ionized by being protonated or deprotonated in reactions with matrix molecules or matrix ions in the dense plasma. The plasma cloud expands into the vacuum in a few hundred nanoseconds, while all the molecules are continuously accelerated by friction in the expanding plasma, and undergoes strong adiabatic cooling in the expanding process. At some point in time during the expansion, the gas molecules cease to be in contact with each other: thereafter the ionization state of the molecules in the plasma cloud is frozen. The degree of ionization of the analyte molecules in conventional MALDI is reported to amount to only around $10^4$. The analyte ions are predominantly singly charged. This process is a "soft ionization" because the analyte molecules are ionized as molecular ions without suffering breaking of bonds.

The ionization of the analyte molecules by the matrix is a function of the energy density in the laser spot, and this function is extremely nonlinear (according to several concurring literature references, the degree of ionization increases with the sixth to seventh power of the energy density). The first analyte ions appear at an energy density threshold of around 10 millijoules per square centimeter. At around 100 millijoules per square centimeter, at least a million times more ions are created; but this energy density constitutes an upper limit for a soft ionization, beyond which spontaneous fragmentations of the analyte molecules occur. The setting of the optimum energy density is critical because, on the one hand, the mass resolution of the time-of-flight mass spectrometer depends on the energy density and, on the other hand, only a maximum of around a thousand analyte ions may be produced per laser pulse. Otherwise the saturation limit of the ion detector system, which is usually equipped with an 8-bit DAC, is exceeded. For the analyses, it is important that individual ions can also be detected with certainty; with a maximum of a thousand ions in the strongest ion signal and a measuring rate of four gigahertz, the ions of the strongest ion signal are distributed over several measuring intervals in such a way that saturation is just avoided, but individual ions still generate detectable signals. Since a doubling of the energy density increases the degree of ionization of the analyte molecules by at least a factor of $2^6=64$, this optimum energy density is only a factor of about 2.5 to 3.0 above the energy density threshold where the first ions appear. Total energy and energy density must be kept constant to about one percent; this keeps fluctuations in ion generation and in the degree of ionization at around 6 to 7 percent. A further increase in the energy density by a factor of 3 would be able to increase the degree of ionization for analyte molecules to more than 10 percent, but would hopelessly oversaturate the ion detector system. Furthermore, increasing the energy density causes a simultaneous increase in the number of "metastable" ions; these are ions that decay on their way to the ion detector and cannot reach the ion detector for ion-optical reasons. If the number of metastable ions becomes too high, the degree of ionization can still increase, but the number of detectable ions cannot.

The MALDI process is complex, and is affected by numerous factors, some of which are interdependent. Since the MALDI method was first published in 1988, many parameters have been investigated and varied. In spite of this, the processes in the matrix and in the vaporization cloud which lead to the ionization of the analyte molecules are still not completely understood and remain the subject of intensive research, see for example the paper by K. Dreisewerd, Chem. Rev. 103 (2003), 395-425: entitled "The Desorption Process in MALDI".

The chemical parameters of the MALDI process, for example the type of matrix substances, the concentration ratio between matrix and analyte molecules, and the preparation conditions, have been thoroughly researched. For analyte molecules of different chemical substance classes, such as proteins or nucleic acids, over a hundred different chemical matrix substances have been elucidated, such as sinapic acid, DHB (2,5-dihydroxybenzoic acid), CHCA (α-cyano-4-hydroxycinnamic acid) or HPA (3-hydroxypicolinic acid), which affect the MALDI process in different ways and can be used for different purposes. The matrix substances are usually aromatic acids; the aromatic ring gives them a strong absorption capacity in the wavelength range between 330 and 360 nanometers, and as acids they can easily donate a proton.

A MALDI sample can be prepared in a number of different ways, for example with "dried droplet" preparation, or the more preferable thin-layer preparation. In "dried droplet" preparation, the matrix substance is dissolved together with the analyte molecules in a solvent before being applied to a sample support and then dried. This preparation distributes analyte molecules extremely inhomogeneously in the matrix crystal complexes, however, and can scarcely be used for quantitative analyses. With thin-layer preparation, on the other hand, the matrix substance is applied to the sample support without analyte molecules and is dried to give a thin polycrystalline matrix layer only a few micrometers thick. This thin matrix layer has a high absorptivity for peptides and proteins. A drop of an aqueous solution containing analyte molecules is then applied to the thin matrix layer; the drop spreads quickly over the whole thin layer, and the analyte molecules are uniformly absorbed. The water can even be removed. After final drying, special measures can be applied to partially redissolve the matrix layer, and the analyte molecules can be embedded uniformly in the matrix layer during the subsequent drying.

As far as the physical parameters of the MALDI process are concerned, investigations have so far chiefly focused on examining how ionization and fragmentation are influenced by the temporal duration of the laser pulses, the intensity in the laser spot and the wavelength of the pulsed laser beam. Spontaneous fragmentations primarily occur only at high energy densities in the first nanosecond, for example; in contrast, most metastable ions are produced by irradiations with durations of longer than three nanoseconds.

Nowadays, commercially available MALDI mass spectrometers are predominantly equipped with pulsed laser systems in the ultraviolet spectral range (UV). Due to its limited lifetime, the low-cost nitrogen laser, with a wavelength of $\lambda=337$ nm, has mostly been replaced by frequency-tripled Nd:YAG lasers, with a wavelength of $\lambda=355$ nm, in high-quality MALDI mass spectrometers. The Nd:YAG laser is based on a YAG crystal (yttrium-aluminum-garnet: $Y_3Al_5O_{12}$) doped with neodymium ions. In the Nd:YAG laser, the frequency of the strongest laser line, which appears at a wavelength of 1064 nanometers, is first doubled to the second harmonic frequency in a first nonlinear optical conversion crystal, producing green light, and then converted into the stated UV wavelength of the third harmonic frequency in a second nonlinear conversion crystal by mixing fundamental wavelength and second harmonic frequency. So-called phase matching must be fulfilled in both crystals, which is achieved by precise temperature control of the crystals to better than 0.1 degree Kelvin. For this purpose, each of the crystals is enclosed in an appropriately controlled oven. As is usual, the second conversion crystal is arranged in such a way that it compensates for the walk-off of the green light with respect to the fundamental wavelength in the first non-linear conversion crystal as far as possible. The duration of the laser pulses used in the MALDI method is typically between 3 and 8 nanoseconds in the UV.

When the nitrogen lasers were replaced with Nd:YAG lasers, the degree of ionization of the analyte molecules surprisingly dropped dramatically, which initially could not be explained. Investigations by the applicant showed that the lower degree of ionization was connected with the transition from an erratic beam structure which is constantly changing over time in the beam profile of the nitrogen laser to an unmodulated and constant Gaussian profile of the Nd:YAG laser. The spatially and temporally modulated beam structure of the nitrogen laser was generated by lightning-like discharges in the nitrogen gas imaged onto the sample, and the form and position of these discharges changed from shot to shot. The solid-state laser, in contrast, delivered a circular beam with a Gaussian profile. The ion yield from a Gaussian profile spot with a diameter of around 100 micrometers was extremely low and had to be compensated for by increasing the energy density; but this caused a deterioration in the mass resolution and an enormous increase in sample consumption, partly because liquefied matrix material was splashed away during the desorption process. It was shown that a spot diameter of only five to ten micrometers improved the degree of ionization; but, kept below the fragmentation limit for the energy density, it supplied too few ions per laser shot. Suitable measures were therefore employed to generate a structured beam profile, which was imaged onto the sample as a spot pattern with around ten intensity peaks, each roughly 6 to 10 micrometers in diameter. This pattern generation led to a dramatic improvement. It was possible to achieve an increase in the degree of ionization of analyte molecules by a factor of 100 without saturation of the ion detector system and with extremely low sample consumption. The structured beam profile for the spot pattern can be generated by many means, such as the introduction of phase disturbances for transversely coherent beams (using crumpled plastic films, for example). The most uniform spot patterns are generated by commercially available lens arrays made of silica glass. The method of beam generation and the corresponding laser systems have been described in U.S. Pat. No. 7,235,781, which is hereby incorporated by reference.

When generating the spot pattern, it is important that all the individual spots have as nearly as possible the same energy density. If, for example, a square lens array made up of nine lenses is irradiated by a laser beam with Gaussian profile, the central lens will produce a spot with higher energy density due to the maximum in the Gaussian profile. If the energy density is increased here by 50 percent, the degree of ionization increases by more than a factor of 10, which makes the other spots of the pattern insignificant for the production of ions. If all the spots are to have approximately the same ionization, only a small, central part of the Gaussian profile of a greatly expanded laser beam can be used for the illumination of the lens array. The light in the remaining part of the Gaussian profile, by far the largest part of the painstakingly generated UV light, must be destroyed with the aid of diaphragms or other measures. Furthermore, the adjustment of the laser beam transverse to the pattern generator is very demanding.

When commercial MALDI time-of-flight mass spectrometers were in their infancy, laser pulse rates of 20 to 50 Hz were used because the nitrogen lasers could not be operated with higher pulse rates without dramatically reducing the number of shots during their life. A good mass spectrum is comprised of a several hundred to a thousand individual spectra; the acquisition of a good, low-noise mass spectrum from a thousand individual spectra thus took around 20 seconds. The switch to solid-state lasers soon allowed pulse rates of 1000 hertz and acquisition times of around one second. With the introduction of imaging mass spectrometry on thin tissue sections with several tens of thousands of pixels and a summed-up mass spectrum for each pixel, the desire for higher acquisition rates was soon voiced, but this requires laser systems with far greater power. In principle, the limit for the laser pulse rate in time-of-flight mass spectrometers is around 10 kilohertz because the 100 microseconds available for the acquisition of a single flight time spectrum are just about sufficient. In order to achieve laser pulse rates of 10 kilohertz, it is advisable to be careful with the laser energy and not destroy most of the UV light produced, because otherwise the high power demands would make the laser systems far too expensive and complex.

There is a need for a mass spectrometer with a low costs laser system for the ionization of a sample which can be operated with particularly high pulse rate, allows the ionization yield to be increased, has a long lifetime and can be operated with low energy consumption.

SUMMARY OF THE INVENTION

A mass spectrometer with a laser desorption ion source includes a pulsed solid-state laser system, conversion crystals to increase the frequency, and a pattern generator in the laser beam. A beam-shaping element is located between the solid-state laser system and the conversion crystals. The beam-shaping element converts the circular laser beam with Gaussian profile into a beam with approximately rectangular cross-section and an approximately homogeneous energy density across the whole rectangular cross-section.

An infrared solid-state laser system may be used. Economic advantages can be realized, for example, by the fact that, firstly, beam-shaping elements for infrared light cost significantly less than beam-shaping elements for ultraviolet light; secondly, the nonlinear conversion crystals can be utilized better and with a higher conversion rate due to the rectangular cross-section and the homogeneous energy density; thirdly, the lifetime of the conversion crystals increases; and fourthly, the beam has a cross-section at the exit of the conversion crystals which has a homogeneous energy density in a square middle section containing more than 90 percent of the beam energy. It is thus ideal for homogeneous illumination of the pattern generator without substantial parts of this higher-energy light having to be cut off and destroyed.

Thus, a mass spectrometer with a pulsed UV laser system is proposed, with relatively low energy consumption, which produces a spatially distributed spot pattern with peaks of uniform energy density on the sample, increasing the degree of ionization for analyte ions as compared to conventional spot patterns. The spot pattern with peaks of uniform energy density can be produced by homogeneous illumination of a pattern generator, for example a lens array. The homogeneous illumination can be generated by a low-cost beam-shaping element, which does not act on the UV beam but on the original infrared beam, in conjunction with changes to the beam cross-section and beam profile brought about by the nonlinear conversion crystals. This beam shaping not only produces a beam profile that illuminates the pattern generator homogeneously with low losses, but at the same time increases the efficiency of the frequency multiplication and the lifetime of the conversion crystals so that significant cost savings are achieved because less laser energy is required and the lifetime is increased.

The beam profile generated by the pattern generator (e.g., for example a structure with nine individual small-diameter spots in a square arrangement) can then be imaged in reduced size onto the sample via a telescope with downstream lens optics. In this example, nine spots with diameters of around five micrometers and identical energy densities can be generated.

The invention thus provides a mass spectrometer with a laser system with a long lifetime that generates a spatially distributed spot pattern on the sample with relatively low energy losses, achieving a high degree of ionization for analyte ions.

These and other objects, features and advantages of the present invention will become more apparent in light of the following detailed description of preferred embodiments thereof, as illustrated in the accompanying drawings.

DETAILED DESCRIPTION OF THE INVENTION

Figure 1:
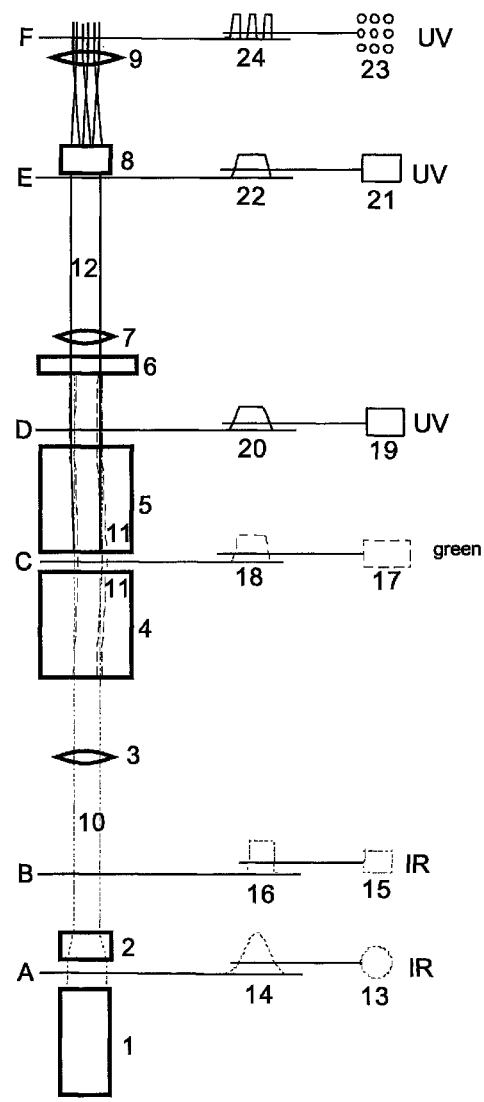
FIG. 1 shows, in the left column, the components 1 to 9 which are necessary for the generation of a structured UV beam, their optical arrangement and the image planes A to F; next to this are shown the intensity profiles of the infrared, green or ultraviolet light in the image planes transverse to the respective laser beam; and in the right column are the shapes of the beam cross-sections, shown for heights of equal intensity. The beam generator 1 contains pump diodes and resonator with laser crystal and, if applicable, a Pockels cell; this is where the temporally pulsed infrared beam 10 is generated. The beam-shaping optical device 2 converts the circular beam with Gaussian profile 13, 14 into a rectangular beam 15 of around 5 by 6 square millimeters with a profile 16 of constant energy density, which is formed in the image plane B. Lens 3 images the image plane B into the image plane C, reduced in size to around 500 by 600 square micrometers; the reduction is not reproduced in FIG. 1 for the sake of clarity. The distances here are not true to scale but greatly shortened for ease of illustration; the rectangular cross-section of the beam of 500 by 600 square micrometers continues almost unchanged through the two temperature-controlled conversion crystals 4 and 5. In the nonlinear crystal 4, frequency doubling creates green light 11, which is deflected laterally at a small angle (walk-off) by the birefringence, and exits with an offset of around 100 micrometers. Between the two conversion crystals, the green light has an energy density profile 18, transverse to the beam, which is almost trapezoidal, the sides of the trapezoid being slightly curved due to the drop in the energy density of the infrared beam along the conversion crystal 4. In the appropriately oriented nonlinear crystal 5, the green beam is steered back to the infrared beam 10 and reacts with it to form the ultraviolet beam 12, which again has a trapezoidal energy density profile 20, but here the sides have less curvature. The infrared light 10 and the green light 11 are masked in the filter 6 so that only the ultraviolet light 12 is transmitted. Lens 7 images the image plane D in enlarged form into the image plane E, which is formed by the surface of the beam splitter 8; here an approximately rectangular section, measuring around 4 by 4 square millimeters, of the cross-section 21 has a homogeneously uniform intensity 22. The beam splitter 8, for example a lens array with short focal length, is illuminated by the homogeneous part of the cross-section, and forms the desired beam pattern from it, in which the spots have the same intensity. A lens 9 then generates a parallel beam with cross-sectional pattern 23 and energy density profile 24 in the plane F. This beam is then imaged onto the sample in reduced size via suitable optics, as can be seen in FIG. 2.

A mass spectrometer comprises a laser system with a pulsed infrared solid-state laser system 1, two conversion crystals 4 and 5 for tripling the frequency, and a pattern generator 8 in the ultraviolet laser beam. A low-cost beam-shaping optical device is located between the pulsed solid-state laser system and the conversion crystals 4 and 5. This beam-shaping optical device converts the circular infrared beam with Gaussian profile 14 into a beam 10 of approximately rectangular shape 15 with approximately the same energy density everywhere. The laser system preferably generates an infrared beam, whose frequency is tripled to supply UV light with a wavelength of between about 300 and 450 nanometers, preferably between about 330 and 370 nanometers.

The laser light beam is converted into a beam with homogeneous energy density, in order to allow homogeneous illumination of the pattern generator. That is, one consciously refrains here from generating a UV laser light beam with a Gaussian profile in the conventional way. Beam-shaping optical devices for UV beams must be manufactured from clean, UV-transmitting materials, preferably silica glass, and they are extremely expensive because the materials are difficult to machine.

Beam-shaping optical devices 2 for an infrared beam are less costly, in contrast. There are various refractive and diffractive beam-shaping optical devices on the market, which are all based on distributing laser light from the center of the Gaussian distribution into the periphery, while maintaining the parallel beam with as high a quality as possible. This can be achieved using refraction with specially shaped lenses. Diffractive beam-shaping elements are slightly more expensive, but usually provide qualitatively better beam shapes. The beam-shaping elements allow the circular infrared beams with a diameter of for example, around 5 millimeters and Gaussian energy distribution to be converted into rectangular beam cross-sections with selectable dimensions of about 5 by 6 square millimeters, for example, and homogeneous energy density.

Figure 2:
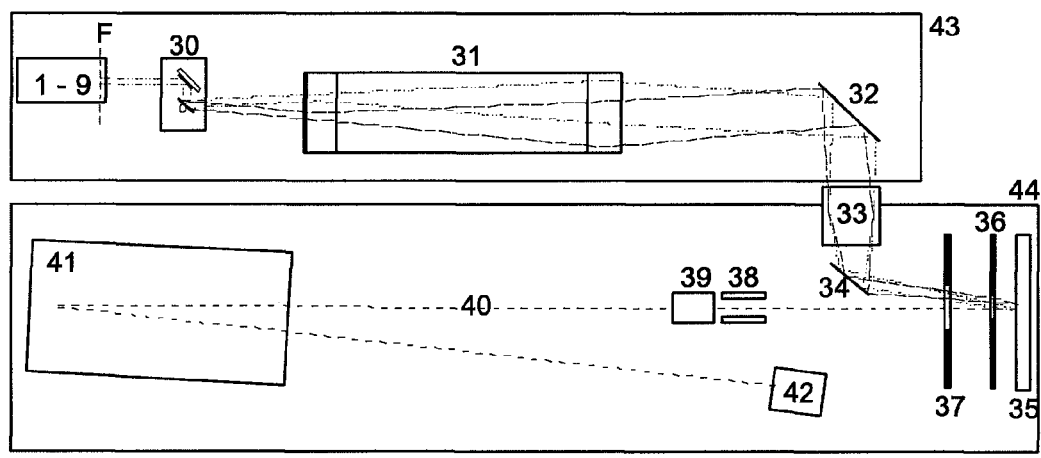
FIG. 2 shows how the assembly 1-9 of all the optical elements 1 to 9 from FIG. 1 is schematically embedded into a laser system 43, which is connected to a MALDI time-of-flight mass spectrometer 44. This is a laser system which controls the position of the laser light pattern on the sample support plate 35 by a rotatable mirror system 30. The parallelized UV laser beam with structured profile from plane F can be slightly deflected in both spatial directions in the rotatable mirror system 30 with two galvo mirrors. The deflected laser beam is then expanded in a Kepler telescope 31 and shifted in parallel in accordance with the angular deflection. The mirror 32 directs the exiting laser beam centrally into the objective lens 33 again, with reduced angular deflection. Depending on the angular deflection, the beam passes through the objective lens 33 centrally but at slightly different angles, thus shifting the position of the spot pattern on the sample support plate 35. The ions generated in the plasma clouds of the laser spot pattern are accelerated by voltages applied to the diaphragms 36 and 37, and form an ion beam 40; this ion beam passes through the two deflection capacitors 38 and 39, which are rotated by 90°, for a trajectory correction, and is focused in the reflector 41 onto the detector 42.

A preferred embodiment is illustrated in FIG. 1. The left column of FIG. 1 shows the components 1 to 9 for generating a structured UV beam. The image planes A to F are shown in addition to the optical arrangement of the components. Next to this, in a second column, the energy density profiles, i.e., the intensity distributions transverse to the respective laser beam, are shown for the image planes A to F. In the right-hand column of FIG. 1, the beam cross-sections of the infrared, green and ultraviolet light are shown with a freely chosen (i.e. not true to scale) intensity. The beam generator 1 contains pump diodes, resonator with laser crystal and, if required, a Pockels cell and a beam attenuator also; this is where the pulsed infrared beam is generated. The beam-shaping optical device 2 converts the beam with circular cross-section 13 and Gaussian profile 14 into a rectangular beam with cross-section 15 and the rectangular profile 16 of approximately the same intensity across the whole cross-section, which is shown for the image plane B. Lens 3 images the image plane B into the image plane C. The distances here are not shown true to scale but greatly shortened for the sake of clarity; the rectangular cross-section of the beam, reduced to around 500 by 600 square micrometers, continues without any significant changes through both conversion crystals 4 and 5. Green light 11 is generated in the nonlinear crystal 4 by frequency doubling, and this green light propagates with a small angle of lateral deflection. This deflection is called "walk-off"; on exiting the around 15 millimeter long conversion crystal 4, the green beam is shifted in comparison to the infrared beam by around 100 micrometers. As is known in the prior art, this walk-off is steered back in the appropriately cut and arranged nonlinear crystal 5 with a walk-off compensation and reacts with the remaining infrared beam 10 to form the ultraviolet beam 12. The necessary phase matching for the deflections for the two nonlinear conversion crystals are set by precise temperature control; the temperature control ovens are not shown in FIG. 1. The remaining infrared light 10 and the remaining green light 11 are masked in the filter 6 so that only the ultraviolet light 12 is transmitted. As is shown for image plane D, the UV beam formed has an approximately trapezoidal intensity profile 20 with slightly curved sides, while the base line of the trapezoid is larger than the top line by an amount which corresponds to around twice the walk-off. In the center part of the cross-section there is a roughly square section of around 500 by 500 square micrometers with homogeneously uniform energy density. The lens 7 images the image plane D in enlarged form onto the surface of the pattern generator 8 (image plane E), which is uniformly illuminated with the square section of the homogeneous energy density. Only a small proportion of the UV beam's energy of around 5 to 10 percent below the side lines of the trapezoid is lost in the illumination. The pattern generator 8, with its lenses of short focal length, shapes the desired beam pattern, in which all the spots have approximately the same intensity. A further lens 9 images the focal points of the lenses of the pattern generator 8 into infinity. In the image plane F, the parallel beam has the desired cross-sectional pattern 23 with the profile 24 of the same energy densities in the spots of the pattern. This beam is then imaged, as can be seen in FIG. 2, onto the sample in reduced size via the appropriate optics.

Due to the exponential decrease of the energy density in the infrared beam 10 within the conversion crystal 4, the cross-section 17 of the green light has a trapezoidal profile 18 with slightly curved side lines; this shape, and the process of reverse compensation in the conversion crystal 5, results in the cross-section 19 of the UV beam also having a trapezoidal profile 20 with slightly curved side lines, although the curvature is less pronounced.

The rectangular cross-section 15 and the homogeneous energy density profile 16 of the infrared beam enable the two nonlinear conversion crystals 4 and 5 to produce a better conversion; and in the image plane D at the exit of the conversion crystals, the UV beam has a cross-section 19 which has an approximately trapezoidal profile 20 with a square center part of homogeneous energy density. While theoretically a maximum of 43 percent of an infrared beam with Gaussian profile can be converted into UV light, it is possible to achieve a higher conversion rate with homogeneous rectangular profiles. For a Gaussian profile, the energy density in the maximum of the beam cross-section is just below the destruction limit for the crystal, which reduces its lifetime. For the rectangular profile, in contrast, the energy density is significantly lower; thus increasing the lifetime of the nonlinear conversion crystals. If the laser system is required to be operated at ten kilohertz pulse frequency for around a year, the lifetime of the laser system must be $10^{11}$ laser pulses. Since the lifetime is essentially determined by the conversion crystals, the rectangular infrared beam is beneficial in terms of cost here also.

The beam pattern of the pattern generator 8, for example the square structure 23 with nine individual partial beams of small diameter, is then imaged via the lens 9 into infinity. As can be seen in FIG. 2, this beam pattern is expanded by a telescope 31 and imaged onto the sample by lens optics 33, where nine spots, each with a diameter of around five micrometers and the same energy density, can be generated, for example. FIG. 2 also depicts how positional control of the spot pattern on the MALDI sample can be achieved with the aid of a double rotatable mirror system 30.

Figure 3:
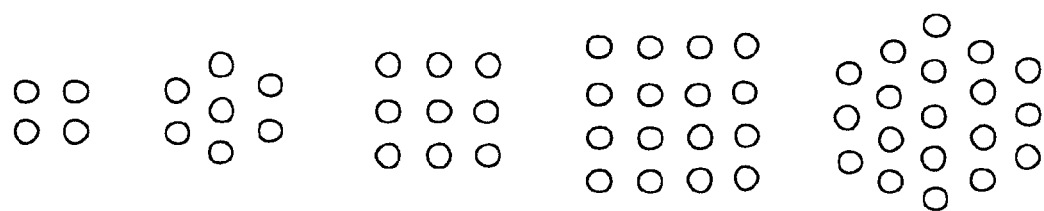
FIG. 3 depicts different regular laser spot patterns with 4, 7, 9, 16 and 19 individual laser spots. The separations between the spots here are just about as large as the spot diameters, but it is also possible to generate patterns with other separations and spot diameters. Pattern generators for square patterns with 4, 9, 16 or also 25 spots can be illuminated with relatively low losses by square forms of the infrared beam and the thus generated square, flat-top profile of the UV beam.

Instead of the nine spots, it is also possible to generate other patterns of 4, 7, 9, 16 or 19 (or 25 or even more) spots, for example, as shown in FIG. 3. The separations and diameters of the spots on the sample can also be varied, although the type of imaging with the optical lens system 33, which is necessarily far removed from the sample, can only achieve, by theory, a minimal diameter of around four to five micrometers. If a change to other spot patterns is desirable, different pattern generators 8 can be introduced into the laser beam with the aid of a mechanical system, such as to be found in a slide projector. For a high degree of ionization, the individual spots on the sample should always have diameters which are smaller than 10 micrometers.

As has been explained in the introduction, although the aim is to increase the degree of ionization for the analyte molecules in order to increase the ion yield, as a rule the number of metastable ions should be limited at the same time. For most investigations, spontaneous fragmentations should be avoided. Furthermore, one has to ensure that no more than around a thousand analyte ions are generated per laser shot in order to avoid saturation of the ion detector system. The prerequisites for the simultaneous fulfillment of these differing requirements are not completely known; there are indications, however, that a pattern of nine spots, each about five micrometers in diameter, comes close to an optimum for the most common methods of preparing the matrix layers and for most analytical goals. For other types of preparation or for other analytical goals, it is sometimes necessary to select other patterns. The yield of analyte ions can probably be increased, with the aid of suitable patterns, to around ten percent of the analyte molecules, i.e., to around a thousand times the yield of the conventional MALDI method. Analytical goals deviating from the norm can require spontaneous fragmentations (for in-source dissociation, ISD) or high proportions of metastable ions (for daughter ion spectra with post-source dissociation, P SD), for example.

The laser system of the mass spectrometer is not only advantageous due to its energy savings and its high yield of analyte ions, but it is also particularly advantageous because the formation of the pattern with very small spots also suppresses the splashing of liquefied matrix material during the desorption, which saves sample material. Especially in the case of a large number of samples per unit of time, as is possible with lasers of high pulse frequency in MALDI-TOF spectrometers, the reduced contamination of the ion optics is an enormous advantage. A further advantage is also that the front of the adiabatically expanding plasma cloud of the pattern accelerates the ions preferentially into the flight direction of the time-of-flight mass spectrometer.

Different types of mass spectrometer may be used. The analyte ions which are produced with the laser system can preferably be detected and analyzed in a special MALDI time-of-flight mass spectrometer with axial ion injection, as depicted schematically in FIG. 2. It is also possible to feed the analyte ions to different types of mass analyzer for the analysis, such as time-of-flight mass spectrometers with orthogonal ion injection (OTOF-MS), ion cyclotron resonance mass spectrometers (ICR-MS), RF ion trap mass spectrometers (IT-MS) or electrostatic ion trap mass spectrometers of the Kingdon type, for example.

The example embodiments cited do not represent a definitive list. With knowledge of this invention, those skilled in the art can design further advantageous embodiments of mass spectrometers with laser systems which are to be covered by the scope of protection of the patent claims.

Therefore, while the invention has been shown and described with reference to a number of embodiments thereof, it will be recognized by those skilled in the art that various changes in form and detail may be made herein without departing from the spirit and scope of the invention as defined by the appended claims.

Although the present invention has been illustrated and described with respect to several preferred embodiments thereof, various changes, omissions and additions to the form and detail thereof, may be made therein, without departing from the spirit and scope of the invention.

What is claimed is:

1. A mass spectrometer comprising a laser desorption ion source having a laser system for the ionization of a sample by matrix-assisted laser desorption, comprising:
   a pulsed solid-state laser system;
   conversion crystals for increasing the frequency, and a pattern generator in the frequency-increased laser beam, wherein
   a beam-shaping optical device is located between the solid-state laser system and the conversion crystals, which converts the pulsed laser beam having a Gaussian profile into an approximately rectangular beam with approximately homogeneous energy density.

2. The mass spectrometer of claim 1, wherein the solid-state laser system generates a pulsed infrared beam and the conversion crystals increase the frequency of the laser light by a factor of three resulting in a UV laser wavelength in the range between about 300 and 450 nanometers.

3. The mass spectrometer of claim 1, wherein the beam-shaping optical device comprises a lens operating with refraction.

4. The mass spectrometer of claim 1, wherein the beam-shaping optical device comprises an diffractive optical device.

5. The mass spectrometer of claim 1, comprising two non-linear conversion crystals to increase the beam frequency, operating with walk-off compensation.

6. The mass spectrometer of claim 1, comprising a pattern generator generating a spot pattern with one of 4, 7, 9, 16, 19, and 25 spots.

7. The mass spectrometer of claim 6, wherein the pattern generator comprises a lens array.

8. The mass spectrometer of claim 6, comprising a telescope and an optical lens system, which image the spot pattern onto the sample.

9. The mass spectrometer of claim 8, wherein the spots on the sample have diameters of about 10 micrometers at most.

10. The mass spectrometer of claim 8, further comprising a rotatable mirror system located between the pattern generator and the telescope, which can be used to control the spot positions on the sample.

11. The mass spectrometer of claim 1, wherein the laser system is configured to generate a sequence of laser light pulses with a pulse rate in the range of about 1 to 10 kHz.

12. A laser system for the ionization of a sample by matrix-assisted laser desorption in a mass spectrometer, with a pulsed solid-state laser system, conversion crystals to increase the frequency, and a pattern generator in the frequency-increased laser beam, comprising a beam-shaping optical device between the solid-state laser system and the conversion crystals, which converts the pulsed laser beam having a Gaussian profile into an approximately rectangular beam with approximately homogeneous energy density.

13. A method for the ionization of a sample by matrix-assisted laser desorption in a mass spectrometer, comprising:
   providing a sample with analyte molecules; and
   ionizing the analyte molecules with a laser system for the ionization of a sample by matrix-assisted laser desorption in a mass spectrometer, with a pulsed solid-state laser system, conversion crystals to increase the frequency, and a pattern generator in the frequency-increased laser beam, comprising a beam-shaping optical device between the solid-state laser system and the conversion crystals, which converts the pulsed laser beam having a Gaussian profile into an approximately rectangular beam with approximately homogeneous energy density, and subsequently measuring the ionized analyte molecules mass-spectrometrically.

* * * * *

UNITED STATES PATENT AND TRADEMARK OFFICE
CERTIFICATE OF CORRECTION

PATENT NO. : 8,431,890 B1  
APPLICATION NO. : 13/656284  
DATED : April 30, 2013  
INVENTOR(S) : Haase et al.

Page 1 of 1

It is certified that error appears in the above-identified patent and that said Letters Patent is hereby corrected as shown below:

On the title page
Item (30), please add "Foreign Application Priority Data – October 19, 2011 (DE) 10 2011 116 405.0"

Signed and Sealed this
Thirteenth Day of January, 2015

Michelle K. Lee
*Deputy Director of the United States Patent and Trademark Office*